(12) United States Patent
Meunier et al.

(10) Patent No.: US 9,408,386 B2
(45) Date of Patent: Aug. 9, 2016

(54) USE OF SUCCINATE DEHYDROGENASE INHIBITORS (SDHIS) FOR CONTROLLING WOOD DISEASES IN GRAPE

(71) Applicants: BAYER CROPSCIENCE AG, Monheim (DE); BAYER INTELLECTUAL PROPERTY GMBH, Monheim (DE)

(72) Inventors: Lucien Meunier, Champagne Au Mont d'or (FR); Gilbert Labourdette, Paray le Monial (FR); Helene Lachaise, Lyons (FR)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/379,501

(22) PCT Filed: Feb. 19, 2013

(86) PCT No.: PCT/EP2013/053292
§ 371 (c)(1),
(2) Date: Aug. 19, 2014

(87) PCT Pub. No.: WO2013/124275
PCT Pub. Date: Aug. 29, 2013

(65) Prior Publication Data
US 2015/0057318 A1 Feb. 26, 2015

(30) Foreign Application Priority Data
Feb. 22, 2012 (EP) .................... 12156448

(51) Int. Cl.
*A01N 43/40* (2006.01)
*A01N 43/56* (2006.01)
*A01N 45/02* (2006.01)
(52) U.S. Cl.
CPC ............ *A01N 43/40* (2013.01); *A01N 43/56* (2013.01); *A01N 45/02* (2013.01)
(58) Field of Classification Search
CPC .................................................. A01N 43/40
See application file for complete search history.

(56) References Cited

FOREIGN PATENT DOCUMENTS

| EP | 2100506 A2 | 9/2009 |
| WO | WO 2004/016088 | * 2/2004 |
| WO | 2010086103 A2 | 8/2010 |
| WO | 2010091803 A2 | 8/2010 |

OTHER PUBLICATIONS

Anco, D.J. et al., "Phomopsis cane and leaf spot of grape," The Ohio State University Extension Fact Sheet, HYG-3031-11 (2011).*
CABA abstract 2001:3293 (2001).*
LUNA Privilege product label, Feb. 2, 2012.*
Fischer et al., "Esca and Fungizide" Der badische Winzer. Rebschutz. pp. 17-19, Oct. 2007.
Di Marco et al., "The control of esca: status and perspective" Phytopathol. Mediterr. vol. 39: 232-240, 2000.
Larignon et al., "Esca et Black Dead Arm: deux acteurs majeurs des maladies du bois chez la Vigne" C.R. Biologies. vol. 332: 765-783, 2009.
Letousey et al., "Early Events Prior to Visual Symptoms in the Apoplectic Form of Grapevine Esca Disease" Phytopathology. vol. 100, No. 5: 425-431, 2010.
International Search Report from corresponding PCT/EP2013/053292, mailed Aug. 6, 2013.
Mugnai et al., "ESCA (Black Measles) and Brown Wood-streaking: Two Old and Elusive Diseases of Grapevines", Plant Disease, American Phytopathological Society, St. Paul, MN, vol. 83, No. 5, May 1, 1999, XP009060374.
Platzer, et al., In vi tro-Wi rkung von Fungiziden auf Fomitiporia mediterranea und Phaeomoniella chlamydospora. die Erreger der Esca-Krankheit der Rebe 11 Mitteilungen Klosterneuburg Rebe Uno Wein Obstbau Undfruechtenverwertung Klosterneuburg. DE, vol. 59, No. 2, Jan. 1, 2009. pp. 74-83, XP009149096.
Adaskaveg et al, Efficacy and timing of fungicides, bactericides and biologicals for decidous tree, fruit, nut, strawberry and vine crops, Jan. 1, 2011, XP055031851.

* cited by examiner

*Primary Examiner* — John Pak
(74) *Attorney, Agent, or Firm* — McBee Moore Woodward Vanik, IP, LLC

(57) ABSTRACT

The invention relates to the use of succinate dehydrogenase SDH inhibitors (SDHIs), in particular bixafen, penflufen or fluopyram for controlling wood diseases in grape, to a method for treating plants or plant parts for controlling wood diseases in grape and to a method for controlling wood diseases in grape plants and plant parts, and in plants which grow from the seedlings, grafts and cuttings, by treating them with SDHIs.

5 Claims, No Drawings

USE OF SUCCINATE DEHYDROGENASE INHIBITORS (SDHIS) FOR CONTROLLING WOOD DISEASES IN GRAPE

CROSS REFERENCE TO RELATED APPLICATIONS

This application is a §371 National Stage Application of PCT/EP2013/053292, filed Feb. 19, 2013, which claims priority to EP 12156448.8, filed Feb. 22, 2012.

BACKGROUND

1. Field of the Invention

The invention relates to the use of succinate dehydrogenase SDH inhibitors (SDHIs), in particular bixafen, penflufen or fluopyram for controlling wood diseases in grape, to a method for treating plants or plant parts for controlling wood diseases in grape and to a method for controlling wood diseases in grape plants and plant parts, in particular roots and in plants which grow from the seedlings, grafts and cuttings, by treating them with SDHIs.

2. Description of Related Art

Wood diseases includes a complex of diseases provoked by the presence of fungal species including *Acremonium* spp., *Botryosphaeria* spp, *Botryosphaeria obtuse*, *Botryosphaeria dothidea*, *Cephalosporium* spp., *Eutypa lata*, *Formitiporia mediteranea*, *Phaemoniella chlamydospora*, *Phaeoacremonium aleophilum*, *Phialophora* spp., *Phomopsis viticola*. *Phomopsis viticola* is responsible for the disease excoriosis, *Eutypa lata* for the disease *Eutypa*, *Botryosphaeria* spp are responsible for Black dead arm disease. Esca is a disease which is caused by at least three fungal species including *Phaeomoniella chlamydospora*, *Phaeoacremonium aleophilum*, and *Fomitiporia mediterranea*. These pathogens were localized in the woody tissues of perennial organs and in lesser proportions in annual canes but never in leaves where symptoms express. The epidemiology is also specific because two forms of symptoms may be distinguished. Chronic symptoms consist of light-green and chlorotic, irregular areas between the veins or along the leaf margin, which gradually spread from the basal to the distal part of the shoot, whereas a more severe form, so-called apoplexy, corresponds to a sudden leaf wilting that leads to death of canes or the whole plant within a few days (Larignon et al, Comptes endus Biologies (2009), 332 (9), pp 765-783). Due to the suddenness of the latter, the causes of the apoplectic form of wood diseases are difficult to investigate and, therefore, less documented. However, the speed of visible symptom development suggests that apoplexy results from early events affecting plant physiology linked to the presence of esca fungi in the wood (P. Letousey et al, Phytopathology (2010), Vol 100 (5), pp 424). Several fungicides and application methods have been described for treating Esca, for example fosetyl-aluminium, penconazole, cyproconazole, tetraconazole (Di Marco et al., Phytopathol. Mediterr, (2000) 39, 232-240). Fluopyram in combination with tebuconazole (Tradename Luna Experience) against *Eutypa lata* is not recommended by the University of California (J Adaskaveg, Report Efficacy and timing of fungicides, bactericides and biologicals for deciduous tree fruit, nut, strawberry, and vine crops (2011)). Wood diseases are difficult to treat as the fungus grows in the woody parts of plant and is therefore not easily accessible for the fungicide. Also systemic fungicides are only of limited use as in most cases they are not evenly distributed throughout the plant. Therefore currently protective treatments, in particular of wounds serving as the entry point for the fungi, are recommended (M Fischer, Der badische Winzer, October 2007, pp 17-19). Consequently there is a need for more efficient treatment of wood diseases in grape.

SUMMARY

It has now been found that, surprisingly, SDHIs, in particular bixafen, penflufen or fluopyram being root, trunk and leaf systemic fungicides are outstandingly suitable for control of wood diseases in grape.

The present inventions relates to the use of SDHIs for the control of wood diseases in grape.

DETAILED DESCRIPTION OF A PREFERRED EMBODIMENT

In one embodiment the present inventions relates to the use of bixafen, penflufen or fluopyram for the control of wood diseases in grape.

In one embodiment the present inventions relates to the use of fluopyram for the control of wood diseases in grape.

In one embodiment the present inventions relates to the use of SDHIs for the control of *Acremonium* spp., *Botryosphaeria* spp, *Botryosphaeria obtuse*, *Botryosphaeria dothidea*, *Cephalosporium* spp., *Eutypa lata*, *Formitiporia mediteranea*, *Phaemoniella chlamydospora*, *Phaeoacremonium aleophilum*, *Phialophora* spp., *Phomopsis viticola* in grape.

In one embodiment the present inventions relates to the use of bixafen, penflufen or fluopyram for the control of *Acremonium* spp., *Botryosphaeria* spp, *Botryosphaeria obtuse*, *Botryosphaeria dothidea*, *Cephalosporium* spp., *Eutypa lata*, *Formitiporia mediteranea*, *Phaemoniella chlamydospora*, *Phaeoacremonium aleophilum*, *Phialophora* spp., *Phomopsis viticola*.

In one embodiment the present inventions relates to the use of fluopyram for the control of *Acremonium* spp., *Botryosphaeria* spp, *Botryosphaeria obtuse*, *Botryosphaeria dothidea*, *Cephalosporium* spp., *Eutypa lata*, *Formitiporia mediteranea*, *Phaemoniella chlamydospora*, *Phaeoacremonium aleophilum*, *Phialophora* spp., *Phomopsis viticola*.

In one embodiment the present inventions relates to the use of SDHIs for the control of *Botryosphaeria* spp, *Botryosphaeria obtuse*, *Botryosphaeria dothidea*, *Eutypa lata*, *Formitiporia mediteranea*, *Phaemoniella chlamydospora*, *Phaeoacremonium aleophilum*, *Phomopsis viticola* in grape.

In one embodiment the present inventions relates to the use of bixafen, penflufen or fluopyram for the control of *Botryosphaeria* spp, *Botryosphaeria obtuse*, *Botryosphaeria dothidea*, *Eutypa lata*, *Formitiporia mediteranea*, *Phaemoniella chlamydospora*, *Phaeoacremonium aleophilum*, *Phomopsis viticola*.

In one embodiment the present inventions relates to the use of fluopyram for the control of *Botryosphaeria* spp, *Botryosphaeria obtuse*, *Botryosphaeria dothidea*, *Eutypa lata*, *Formitiporia mediteranea*, *Phaemoniella chlamydospora*, *Phaeoacremonium aleophilum*, *Phomopsis viticola*.

In one embodiment the present inventions relates to the use of SDHIs for the control of *Botryosphaeria* spp, *Botryosphaeria obtuse*, *Botryosphaeria dothidea*, *Eutypa lata*, *Formitiporia mediteranea*, *Phaemoniella chlamydospora*, *Phaeoacremonium aleophilum*, *Phomopsis viticola* in grape.

In one embodiment the present inventions relates to the use of bixafen, penflufen or fluopyram for the control of *Botryosphaeria* spp, *Botryosphaeria obtuse*, *Botryosphaeria dothidea*, *Eutypa lata*, *Formitiporia mediteranea*, *Phaemoniella chlamydospora*, *Phaeoacremonium aleophilum*, *Phomopsis viticola*.

In one embodiment the present inventions relates to the use of fluopyram for the control of *Botryosphaeria* spp, *Botryosphaeria obtuse*, *Botryosphaeria dothidea*, *Eutypa lata*, *Formitiporia mediteranea*, *Phaemoniella chlamydospora*, *Phaeoacremonium aleophilum*, *Phomopsis viticola*.

In one embodiment the present inventions relates to the use of bixafen, penflufen or fluopyram for the control of *Botryosphaeria* spp, *Botryosphaeria obtuse*, *Botryosphaeria dothidea*, *Eutypa lata*, *Formitiporia mediteranea*, *Phaemoniella chlamydospora*, *Phaeoacremonium aleophilum*, *Phomopsis viticola* in grape.

In one embodiment the present inventions relates to the use of fluopyram for the control of *Botryosphaeria* spp, *Botryosphaeria obtuse*, *Botryosphaeria dothidea*, *Eutypa lata*, *Formitiporia mediteranea*, *Phaemoniella chlamydospora*, *Phaeoacremonium aleophilum*, *Phomopsis viticola* in grape.

In one embodiment the present inventions relates to the use of SDHIs for the control of *Formitiporia mediteranea*, *Phaemoniella chlamydospora*, *Phaeoacremonium aleophilum*, *Phomopsis viticola* in grape.

In one embodiment the present inventions relates to the use of bixafen, penflufen or fluopyram for the control of *Formitiporia mediteranea*, *Phaemoniella chlamydospora*, *Phaeoacremonium aleophilum*, *Phomopsis viticola*.

In one embodiment the present inventions relates to the use of fluopyram for the control of *Formitiporia mediteranea*, *Phaemoniella chlamydospora*, *Phaeoacremonium aleophilum*, *Phomopsis viticola*.

In one embodiment the present inventions relates to the use of bixafen, penflufen or fluopyram for the control of *Formitiporia mediteranea*, *Phaemoniella chlamydospora*, *Phaeoacremonium aleophilum*, *Phomopsis viticola* in grape.

In one embodiment the present inventions relates to the use of fluopyram for the control of *Formitiporia mediteranea*, *Phaemoniella chlamydospora*, *Phaeoacremonium aleophilum*, *Phomopsis viticola* in grape.

In one embodiment the present inventions relates to a method for treating plants or plant parts for controlling wood diseases in grape by treating them with SDHIs.

In one embodiment the present inventions relates to a method for treating plants or plant parts for controlling wood diseases in grape by treating them with bixafen, penflufen or fluopyram.

In one embodiment the present inventions relates to a method for controlling wood diseases in grape plants and plant parts, and in plants which grow from the seedlings, grafts and cuttings, by treating them with SDHIs.

In one embodiment the present inventions relates to a method for controlling wood diseases in grape plants and plant parts, and in plants which grow from the seedlings, grafts and cuttings, by treating them with bixafen, penflufen or fluopyram.

In one embodiment the present inventions relates to a method for treating plants or plant parts for controlling *Acremonium* spp., *Botryosphaeria* spp, *Botryosphaeria obtuse*, *Botryosphaeria dothidea*, *Cephalosporium* spp., *Eutypa lata*, *Formitiporia mediteranea*, *Phaemoniella chlamydospora*, *Phaeoacremonium aleophilum*, *Phialophora* spp., *Phomopsis viticola* in grape by treating them with SDHIs.

In one embodiment the present inventions relates to a method for treating plants or plant parts for controlling *Acremonium* spp., *Botryosphaeria* spp, *Botryosphaeria obtuse*, *Botryosphaeria dothidea*, *Cephalosporium* spp., *Eutypa lata*, *Formitiporia mediteranea*, *Phaemoniella chlamydospora*, *Phaeoacremonium aleophilum*, *Phialophora* spp., *Phomopsis viticola* in grape by treating them with bixafen, penflufen or fluopyram.

In one embodiment the present inventions relates to a method for controlling *Acremonium* spp., *Botryosphaeria* spp, *Botryosphaeria obtuse*, *Botryosphaeria dothidea*, *Cephalosporium* spp., *Eutypa lata*, *Formitiporia mediteranea*, *Phaemoniella chlamydospora*, *Phaeoacremonium aleophilum*, *Phialophora* spp., *Phomopsis viticola* in grape plants and plant parts, and in plants which grow from the seedlings, grafts and cuttings, by treating them with SDHIs.

In one embodiment the present inventions relates to a method for controlling *Acremonium* spp., *Botryosphaeria* spp, *Botryosphaeria obtuse*, *Botryosphaeria dothidea*, *Cephalosporium* spp., *Eutypa lata*, *Formitiporia mediteranea*, *Phaemoniella chlamydospora*, *Phaeoacremonium aleophilum*, *Phialophora* spp., *Phomopsis viticola* in grape plants and plant parts, and in plants which grow from the seedlings, grafts and cuttings, by treating them with bixafen, penflufen or fluopyram.

In one embodiment the present inventions relates to a method for treating plants or plant parts for controlling *Botryosphaeria* spp, *Botryosphaeria obtuse*, *Botryosphaeria dothidea*, *Eutypa lata*, *Formitiporia mediteranea*, *Phaemoniella chlamydospora*, *Phaeoacremonium aleophilum*, *Phomopsis viticola* in grape by treating them with SDHIs.

In one embodiment the present inventions relates to a method for treating plants or plant parts for controlling *Botryosphaeria* spp, *Botryosphaeria obtuse*, *Botryosphaeria dothidea*, *Eutypa lata*, *Formitiporia mediteranea*, *Phaemoniella chlamydospora*, *Phaeoacremonium aleophilum*, *Phomopsis viticola* in grape by treating them with bixafen, penflufen or fluopyram.

In one embodiment the present inventions relates to a method for treating plants or plant parts for controlling *Botryosphaeria* spp, *Botryosphaeria obtuse*, *Botryosphaeria dothidea*, *Eutypa lata*, *Formitiporia mediteranea*, *Phaemoniella chlamydospora*, *Phaeoacremonium aleophilum*, *Phomopsis viticola* in grape by treating them with fluopyram.

In one embodiment the present inventions relates to a method for treating plants or plant parts for controlling *Formitiporia mediteranea*, *Phaemoniella chlamydospora*, *Phaeoacremonium aleophilum*, *Phomopsis viticola* in grape by treating them with SDHIs.

In one embodiment the present inventions relates to a method for treating plants or plant parts for controlling *Formitiporia mediteranea*, *Phaemoniella chlamydospora*, *Phaeoacremonium aleophilum*, *Phomopsis viticola* in grape by treating them with bixafen, penflufen or fluopyram.

In one embodiment the present inventions relates to a method for treating plants or plant parts for controlling *Formitiporia mediteranea*, *Phaemoniella chlamydospora*, *Phaeoacremonium aleophilum*, *Phomopsis viticola* in grape by treating them with fluopyram.

In one embodiment the present inventions relates to a method for controlling *Botryosphaeria* spp, *Botryosphaeria obtuse*, *Botryosphaeria dothidea*, *Eutypa lata*, *Formitiporia mediteranea*, *Phaemoniella chlamydospora*, *Phaeoacremonium aleophilum*, *Phomopsis viticola* in grape plants and plant parts, and in plants which grow from the seedlings, grafts and cuttings, by treating them with SDHIs.

In one embodiment the present inventions relates to a method for controlling *Botryosphaeria* spp, *Botryosphaeria obtuse*, *Botryosphaeria dothidea*, *Eutypa lata*, *Formitiporia mediteranea*, *Phaemoniella chlamydospora*, *Phaeoacremonium aleophilum*, *Phomopsis viticola* in grape plants and plant parts, and in plants which grow from the seedlings, grafts and cuttings, by treating them with bixafen, penflufen or fluopyram.

In one embodiment the present inventions relates to a method for controlling *Botryosphaeria* spp, *Botryosphaeria obtuse, Botryosphaeria dothidea, Eutypa lata, Formitiporia mediteranea, Phaemoniella chlamydospora, Phaeoacremonium aleophilum, Phomopsis viticola* in grape plants and plant parts, and in plants which grow from the seedlings, grafts and cuttings, by treating them with fluopyram.

In one embodiment the present inventions relates to a method for *Formitiporia mediteranea, Phaemoniella chlamydospora, Phaeoacremonium aleophilum, Phomopsis viticola* in grape plants and plant parts, and in plants which grow from the seedlings, grafts and cuttings, by treating them with SDHIs.

In one embodiment the present inventions relates to a method for controlling *Formitiporia mediteranea, Phaemoniella chlamydospora, Phaeoacremonium aleophilum, Phomopsis viticola* in grape plants and plant parts, and in plants which grow from the seedlings, grafts and cuttings, by treating them with bixafen, penflufen or fluopyram.

In one embodiment the present inventions relates to a method for *Formitiporia mediteranea, Phaemoniella chlamydospora, Phaeoacremonium aleophilum, Phomopsis viticola* in grape plants and plant parts, and in plants which grow from the seedlings, grafts and cuttings, by treating them with fluopyram.

DEFINITIONS

In the context of the present invention, "control of wood diseases in grape" means a significant reduction in infestation by *Acremonium* spp., *Botryosphaeria* spp, *Botryosphaeria obtuse, Botryosphaeria dothidea, Cephalosporium* spp., *Eutypa lata, Formitiporia mediteranea, Phaemoniella chlamydospora, Phaeoacremonium aleophilum, Phialophora* spp., *Phomopsis viticola*, compared with the untreated plant, preferably a significant reduction (by 25-50%), compared with the untreated plant (100%), more preferably a significant reduction (by 40-79%), compared with the untreated plant (100%); even more preferably, the infection by *Acremonium* spp., *Botryosphaeria* spp, *Botryosphaeria obtuse, Botryosphaeria dothidea, Cephalosporium* spp., *Eutypa lata, Formitiporia mediteranea, Phaemoniella chlamydospora, Phaeoacremonium aleophilum, Phialophora* spp., *Phomopsis viticola* is entirely suppressed (by 70-100%). The control may be curative, i.e. for treatment of already infected plants, or protective, for protection of plants which have not yet been infected.

In the context of the present invention, a plant is preferably understood to mean a plant at dormancy stage (BBCH 00 according to the BBCH monograph from the German Federal Biological Research Centre for Agriculture and Forestry, 2nd edition, 2001) or after up to the stage of end of leaf fall (BBCH97).

All plants and plant parts can be treated in accordance with the invention.

In the context of the present invention, Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant varieties which are protectable and non-protectable by plant breeders' rights.

In the context of the present invention, the term "plant parts" are to be understood as meaning all above-ground and below-ground parts and organs of plants, such as shoot, leaf, flower and root, by way of example ears, leaves, needles, stalks, stems, trunks, flowers, fruit bodies, fruits, seed (including seeds of transgenic plants), seedlings, root-stocks, grafts and cuttings, and also roots, and rhizomes. The plant parts also include harvested material and also vegetative and generative propagation material, for example root-stocks, cuttings, grafts, rhizomes, slips and seedlings.

Preferred plant parts are leaves, stems, shoots and trunks, very preferred are stems, shoots and trunks.

In the context of the present invention a succinate dehydrogenase (SDH) inhibitor refers to a compound which is capable of inhibiting succinate dehydrogenase in phytopathogenic fungal organisms, also being known as complex II inhibitor. According to the present invention the at least one SDH inhibitor may be selected from the group consisting of bixafen (1.1), penflufen (1.2), sedaxane (1.3), isopyrazam (comprising mixture of syn-epimeric racemate 1RS,4SR,9RS and anti-epimeric racemate 1RS,4SR,9SR, anti-epimeric racemate 1RS,4SR,9SR, anti-epimeric enantiomer 1R,4S,9S, anti-epimeric enantiomer 1S,4R,9R, syn epimeric racemate 1RS,4SR,9RS, syn-epimeric enantiomer 1R,4S,9R, syn-epimeric enantiomer 1S,4R,9S) (1.4), penthiopyrad (1.5), furametpyr (1.6), boscalid (1.7), fluxapyroxad (1.8), N-[1-(1,4-dichlorophenyl)-1-methoxypropan-2-yl]-3-(difluoromethyl)-1-methyl-1H-pyrazole-4-carboxamide (1.9), N-[9-(dichloromethylen)-1,2,3,4-tetrahydro-1,4-methanonaphthalen-5-yl]-3-(difluoromethyl)-1-methyl-1H-pyrazol-4-carboxamide (1.10), N-[(1S,4R)-9-(dichloromethylen)-1,2,3,4-tetrahydro-1,4-methanonaphthalen-5-yl]-3-(difluoromethyl)-1-methyl-1H-pyrazol-4-carboxamide (1.11), N-[(1R,4S)-9-(dichloromethylen)-1,2,3,4-tetrahydro-1,4-methanonaphthalen-5-yl]-3-(difluoromethyl)-1-methyl-1H-pyrazol-4-carboxamide (1.12), 3-(difluoromethyl)-1-methyl-N-[2-(1,1,2,2-tetrafluoroethoxy)phenyl]-1H-pyrazol-4-carboxamide (1.13), 3-(difluoromethyl)-N-[4-fluoro-2-(1,1,2,3,3,3-hexafluoropropoxy)phenyl]-1-methyl-1H-pyrazol-4-carboxamide (1.14), 3-(difluoromethyl)-1-methyl-N-[2-(1,1,2,3,3,3-hexafluoropropoxy)phenyl]-1-methyl-1H-pyrazol-4-carboxamide (1.15), 3-(difluoromethyl)-1-methyl-N-[2-(3-Cl-1,1,2-trifluoroethoxy)phenyl]-1H-pyrazol-4-carboxamide (1.16), N-[9-(dichloromethylene)-1,2,3,4-tetrahydro-1,4-methanonaphthalen-5-yl]-3-(difluoromethyl)-1-methyl-1H-pyrazole-4-carboxamide (1.17), N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide (1.18), and N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide (1.19), fluopyram (1.20).

The SDHIs are described either by the CAS-No or another reference:

Bixafen (1.1; CAS-No 581809-46-3), penflufen (1.2; CAS-No 494793-67-8), sedaxane (1.3; CAS-No 874967-67-6), isopyrazam (comprising mixture of syn-epimeric racemate 1RS,4SR,9RS and anti-epimeric racemate 1RS,4SR,9SR, anti-epimeric racemate 1RS,4SR,9SR, anti-epimeric enantiomer 1R,4S,9S, anti-epimeric enantiomer 1S,4R,9R, syn epimeric racemate 1RS,4SR,9RS, syn-epimeric enantiomer 1R,4S,9R, syn-epimeric enantiomer 1S,4R,9S) (1.4; CAS-No 881685-58-1), penthiopyrad (1.5; CAS-No 183675-82-3), furametpyr (1.6; CAS-No 123572-88-3), boscalid (1.7; CAS-No 188425-85-6), fluxapyroxad (1.8; CAS-No 907204-31-3), N-[1-(1,4-dichlorophenyl)-1-methoxypropan-2-yl]-3-(difluoromethyl)-1-methyl-1H-pyrazole-4-carboxamide (1.9; CAS-No), [9-(dichloromethylen)-1,2,3,4-tetrahydro-1,4-methanonaphthalen-5-yl]-3-(difluoromethyl)-

1-methyl-1H-pyrazol-4-carboxamide (1.10), N-[(1S,4R)-9-(dichloromethylen)-1,2,3,4-tetrahydro-1,4-methanonaphthalen-5-yl]-3-(difluoromethyl)-1-methyl-1H-pyrazol-4-carboxamide (1.11; CAS-No), N-[(1R,4S)-9-(dichloromethylen)-1,2,3,4-tetrahydro-1,4-methanonaphthalen-5-yl]-3-(difluoromethyl)-1-methyl-1H-pyrazol-4-carboxamide (1.12; CAS-No), 3-(difluoromethyl)-1-methyl-N-[2-(1,1,2,2-tetrafluoroethoxy)phenyl]-1H-pyrazol-4-carboxamide (1.13; CAS-No), 3-(difluoromethyl)-N-[4-fluoro-2-(1,1,2,3,3,3-hexafluoropropoxy)phenyl]-1-methyl-1H-pyrazol-4-carboxamide (1.14; CAS-No), 3-(difluoromethyl)-1-methyl-N-[2-(1,1,2,3,3,3-hexafluoropropoxy)phenyl]-1-methyl-1H-pyrazol-4-carboxamide (1.15; CAS-No), 3-(difluoromethyl)-1-methyl-N-[2-(3-Cl-1,1,2-trifluoroethoxy)phenyl]-1H-pyrazol-4-carboxamide (1.16; CAS-No), N-[9-(dichloromethylene)-1,2,3,4-tetrahydro-1,4-methanonaphthalen-5-yl]-3-(difluoromethyl)-1-methyl-1H-pyrazole-4-carboxamide (1.17; CAS-No), N-[(1S,4R)-9-(dichloromethylene)-1,2,3,4-tetrahydro-1,4-methanonaphthalen-5-yl]-3-(difluoromethyl)-1-methyl-1H-pyrazol-4-carboxamide (1.18; CAS-No), and N-[(1R,4S)-9-(dichloromethylene)-1,2,3,4-tetrahydro-1,4-methanonaphthalen-5-yl]-3-(difluoromethyl)-1-methyl-1H-pyrazol-4-carboxamide (1.19; CAS-No).

In the context of the present invention (A) fluopyram (1.20) refers to a compound of the formula

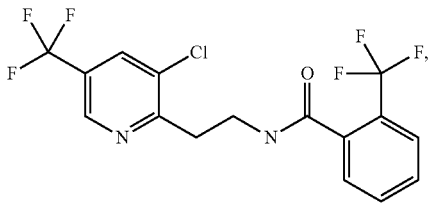

also known as N-{2-[3-chloro-5-(trifluoromethyl)-2-pyridyl]ethyl}-α,α,α-trifluoro-ortho-toluamide or N-[2-[3-chloro-5-(trifluoromethyl)-2-pyridinyl]ethyl]-2-(trifluoromethyl)benzamide Fluopyram is widely known as a fungicide, belonging to the group of succinate dehydrogenase (SDH) inhibitors. WO 2004/016088 discloses derivatives of the pyridinylethyl-benzamide fungicides, for example fluopyram against different phytopathogenic fungi. However, it is not apparent from the teaching of the publication that fluopyram is highly efficient against the wood disease described above. More particularly, the suitability of fluopyram for treatment of wood diseases is not explicitly disclosed.

Preferably the succinate dehydrogenase (SDH) inhibitor may be selected from the group consisting of fluopyram (1.20), bixafen (1.1), penflufen (1.2), sedaxane (1.3), isopyrazam (comprising mixture of syn-epimeric racemate 1RS,4SR,9RS and anti-epimeric racemate 1RS,4SR,9SR, anti-epimeric racemate 1RS,4SR,9SR, anti-epimeric enantiomer 1R,4S,9S, anti-epimeric enantiomer 1S,4R,9R, syn epimeric racemate 1RS,4SR,9RS, syn-epimeric enantiomer 1R,4S,9R, syn-epimeric enantiomer 1S,4R,9S) (1.4), penthiopyrad (1.5), furametpyr (1.6), fluxapyroxad (1.8), N-[1-(1,4-dichlorophenyl)-1-methoxypropan-2-yl]-3-(difluoromethyl)-1-methyl-1H-pyrazole-4-carboxamide (1.9), N-[9-(dichloromethylen)-1,2,3,4-tetrahydro-1,4-methanonaphthalen-5-yl]-3-(difluoromethyl)-1-methyl-1H-pyrazol-4-carboxamide (1.10), N-[(1S,4R)-9-(dichloromethylen)-1,2,3,4-tetrahydro-1,4-methanonaphthalen-5-yl]-3-(difluoromethyl)-1-methyl-1H-pyrazol-4-carboxamide (1.11), N-[(1R,4S)-9-(dichloromethylen)-1,2,3,4-tetrahydro-1,4-methanonaphthalen-5-yl]-3-(difluoromethyl)-1-methyl-1H-pyrazol-4-carboxamide (1.12), 3-(difluoromethyl)-1-methyl-N-[2-(1,1,2,2-tetrafluoroethoxy)phenyl]-1H-pyrazol-4-carboxamide (1.13), 3-(difluoromethyl)-N-[4-fluoro-2-(1,1,2,3,3,3-hexafluoropropoxy)phenyl]-1-methyl-1H-pyrazol-4-carboxamide (1.14), 3-(difluoromethyl)-1-methyl-N-[2-(1,1,2,3,3,3-hexafluoropropoxy)phenyl]-1-methyl-1H-pyrazol-4-carboxamide (1.15), 3-(difluoromethyl)-1-methyl-N-[2-(3-Cl-1,1,2-trifluoroethoxy)phenyl]-1H-pyrazol-4-carboxamide (1.16), N-[9-(dichloromethylene)-1,2,3,4-tetrahydro-1,4-methanonaphthalen-5-yl]-3-(difluoromethyl)-1-methyl-1H-pyrazole-4-carboxamide (1.17), N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide (1.18), and N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide (1.19).

More preferably the succinate dehydrogenase (SDH) inhibitor may be selected from the group consisting of fluopyram (1.20), bixafen (1.1), penflufen (1.2), isopyrazam (comprising mixture of syn-epimeric racemate 1RS,4SR,9RS and anti-epimeric racemate 1RS,4SR,9SR, anti-epimeric racemate 1RS,4SR,9SR, anti-epimeric enantiomer 1R,4S,9S, anti-epimeric enantiomer 1S,4R,9R, syn epimeric racemate 1RS,4SR,9RS, syn-epimeric enantiomer 1R,4S,9R, syn-epimeric enantiomer 1S,4R,9S) (1.4), penthiopyrad (1.5), fluxapyroxad (1.8), N-[1-(1,4-dichlorophenyl)-1-methoxypropan-2-yl]-3-(difluoromethyl)-1-methyl-1H-pyrazole-4-carboxamide (1.9), N-[9-(dichloromethylen)-1,2,3,4-tetrahydro-1,4-methanonaphthalen-5-yl]-3-(difluoromethyl)-1-methyl-1H-pyrazol-4-carboxamide (1.10), N-[(1S,4R)-9-(dichloromethylen)-1,2,3,4-tetrahydro-1,4-methanonaphthalen-5-yl]-3-(difluoromethyl)-1-methyl-1H-pyrazol-4-carboxamide (1.11), N-[(1R,4S)-9-(dichloromethylen)-1,2,3,4-tetrahydro-1,4-methanonaphthalen-5-yl]-3-(difluoromethyl)-1-methyl-1H-pyrazol-4-carboxamide (1.12), 3-(difluoromethyl)-1-methyl-N-[2-(1,1,2,2-tetrafluoroethoxy)phenyl]-1H-pyrazol-4-carboxamide (1.13), 3-(difluoromethyl)-N-[4-fluoro-2-(1,1,2,3,3,3-hexafluoropropoxy)phenyl]-1-methyl-1H-pyrazol-4-carboxamide (1.14), 3-(difluoromethyl)-1-methyl-N-[2-(1,1,2,3,3,3-hexafluoropropoxy)phenyl]-1-methyl-1H-pyrazol-4-carboxamide (1.15), 3-(difluoromethyl)-1-methyl-N-[2-(3-Cl-1,1,2-trifluoroethoxy)phenyl]-1H-pyrazol-4-carboxamide (1.16), N-[9-(dichloromethylene)-1,2,3,4-tetrahydro-1,4-methanonaphthalen-5-yl]-3-(difluoromethyl)-1-methyl-1H-pyrazole-4-carboxamide (1.17), N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide (1.18), and N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide (1.19).

Even more preferably the succinate dehydrogenase (SDH) inhibitor may be selected from the group consisting of fluopyram (1.20), bixafen (1.1), penflufen (1.2), isopyrazam (comprising mixture of syn-epimeric racemate 1RS,4SR,9RS and anti-epimeric racemate 1RS,4SR,9SR, anti-epimeric racemate 1RS,4SR,9SR, anti-epimeric enantiomer 1R,4S,9S, anti-epimeric enantiomer 1S,4R,9R, syn epimeric racemate 1RS,4SR,9RS, syn-epimeric enantiomer 1R,4S,9R, syn-epimeric enantiomer 1S,4R,9S) (1.4), penthiopyrad (1.5), fluxapyroxad (1.8), N-[1-(1,4-dichlorophenyl)-1-methoxypropan-2-yl]-3-(difluoromethyl)-1-methyl-1H-pyrazole-4-carboxamide (1.9), N-[9-(dichloromethylene)-1,2, 3,4-tetrahydro-1,4-methanonaphthalen-5-yl]-3-(difluoromethyl)-1-methyl-1H-pyrazol-4-carboxamide (1.10), N-[(1S,4R)-9-(dichloromethylen)-1,2,3,4-tetrahydro-1,4-methanonaphthalen-5-yl]-3-(difluoromethyl)-1-methyl-1H-pyrazol-4-carboxamide (1.11), N-[(1R,4S)-9-(dichloromethylen)-1,2,3,4-tetrahydro-1,4-methanonaphthalen-5-yl]-3-(difluoromethyl)-1-methyl-1H-pyrazol-4-carboxamide (1.12).

Preferably, at least one SDH inhibitor is selected from the group consisting of bixafen (1.1), penflufen (1.2), and fluopyram (1.20). The most preferred SDH inhibitor is fluopyram (1.20).

Mixtures

SDHIs, in particular fluopyram, bixafen or penflufen may be present in their commercially available formulations and in the use forms, prepared from these formulations, as a mixture with other active ingredients, such as insecticides, attractants, sterilants, bactericides, acaricides, nematicides, fungicides, growth regulators, herbicides, safeners, fertilizers, biological control agents, resistance enhacers or semiochemicals.

In addition, the described positive effect of SDHIs, in particular fluopyram, bixafen or penflufen on the control of wood diseases can be promoted by an additional treatment with insecticidal, fungicidal or bactericidal active ingredients, resistance enhancers and biological control agents.

Combinations of SDHIs, with substances including insecticides, fungicides, resistance enhancers and bactericides, fertilizers, growth regulators and biological control agents, can likewise find use in the control of wood diseases in the context of the present invention. The combined use of fluopyram, with genetically modified cultivars, especially of transgenic vine cultivars, is additionally likewise possible.

Furthermore the SDHIs, in particular bixafen, penflufen or fluopyram according to the present invention may comprise one or more additional fungicides which may be selected from the group consisting of:

(1) Inhibitors of the ergosterol biosynthesis, for example (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulfate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifine (65472-88-0), (1.33) nuarimol (63284-71-9), (1.34) oxpoconazole (174212-12-5), (1.35) paclobutrazol (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafine (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (83657-17-4), (1.58) viniconazole (77174-66-4), (1.59) voriconazole (137234-62-9), (1.60) 1-(4-chlorophenyl)-2-(1H-1,2,4-triazol-1-yl)cycloheptanol (129586-32-9), (1.61) methyl 1-(2,2-dimethyl-2,3-dihydro-1H-inden-1-yl)-1H-imidazole-5-carboxylate (110323-95-0), (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl] 1H-imidazole-1-carbothioate (111226-71-2).

(2) inhibitors of the respiratory chain at complex I or II, for example (2.1) bixafen (581809-46-3), (2.2) boscalid (188425-85-6), (2.3) carboxin (5234-68-4), (2.4) diflumetorim (130339-07-0), (2.5) fenfuram (24691-80-3), (2.6) fluopyram (658066-35-4), (2.7) flutolanil (66332-96-5), (2.8) fluxapyroxad (907204-31-3), (2.9) furametpyr (123572-88-3), (2.10) furmecyclox (60568-05-0), (2.11) isopyrazam (mixture of syn-epimeric racemate 1RS,4SR,9RS and anti-epimeric racemate 1RS,4SR,9SR) (881685-58-1), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil (55814-41-0), (2.19) oxycarboxin (5259-88-1), (2.20) penflufen (494793-67-8), (2.21) penthiopyrad (183675-82-3), (2.22) sedaxane (874967-67-6), (2.23) thifluzamide (130000-40-7), (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide (1092400-95-7) (WO 2008148570), (2.28) 5,8-difluoro-N-[2-(2-fluoro-4-{[4-(trifluoromethyl)pyridin-2-yl]oxy}-phenyl)ethyl]quinazolin-4-amine (1210070-84-0) (WO2010025451), (2.29) N-[9-(dichloromethylene)-1,2,3,4-tetrahydro-1,4-methanonaphthalen-5-yl]-3-(difluoromethyl)-1-methyl-1H-pyrazole-4-carboxamide, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) inhibitors of the respiratory chain at complex III, for example (3.1) ametoctradin (865318-97-4), (3.2) amisulbrom (348635-87-0), (3.3) azoxystrobin (131860-33-8), (3.4) cyazofamid (120116-88-3), (3.5) coumethoxystrobin (850881-30-0), (3.6) coumoxystrobin (850881-70-8), (3.7) dimoxystrobin (141600-52-4), (3.8) enestroburin (238410-11-2) (WO 2004/058723), (3.9) famoxadone (131807-57-3) (WO 2004/058723), (3.10) fenamidone (161326-34-7) (WO 2004/058723), (3.11) fenoxystrobin (918162-02-4), (3.12) fluoxastrobin (361377-29-9) (WO 2004/058723), (3.13) kresoxim-methyl (143390-89-0) (WO 2004/058723), (3.14) metominostrobin (133408-50-1) (WO 2004/058723), (3.15) orysastrobin (189892-69-1) (WO 2004/058723), (3.16)

picoxystrobin (117428-22-5) (WO 2004/058723), (3.17) pyraclostrobin (175013-18-0) (WO 2004/058723), (3.18) pyrametostrobin (915410-70-7) (WO 2004/058723), (3.19) pyraoxystrobin (862588-11-2) (WO 2004/058723), (3.20) pyribencarb (799247-52-2) (WO 2004/058723), (3.21) triclopyricarb (902760-40-1), (3.22) trifloxystrobin (141517-21-7) (WO 2004/058723), (3.23) (2E)-2-(2-{[6-(3-chloro-2-methylphenoxy)-5-fluoropyrimidin-4-yl]oxy}phenyl)-2-(methoxyimino)-N-methylethanamide (WO 2004/058723), (3.24) (2E)-2-(methoxyimino)-N-methyl-2-(2-{[({(1E)-1-[3-(trifluoromethyl)phenyl]ethylidene}amino)oxy]methyl}phenyl)ethanamide (WO 2004/058723), (3.25) (2E)-2-(methoxyimino)-N-methyl-2-(2-{[({(1E)-1-[3-(trifluoromethyl)phenyl]ethoxy}imino)methyl]phenyl}ethanamide (158169-73-4), (3.26) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide (119899-14-8), (3.29) 5-methoxy-2-methyl-4-(2-{[({(1E)-1-[3-(trifluoromethyl)phenyl]ethylidene}amino)oxy]methyl}-phenyl)-2,4-dihydro-3H-1,2,4-triazol-3-one, (3.30) methyl (2E)-2-2-{2-[({cyclopropyl[(4-methoxyphenyl)imino]methyl}sulfanyl)methyl]phenyl}-3-methoxyprop-2-enoate (149601-03-6), (3.31) N-(3-ethyl-3,5,5-trimethylcyclohexyl)-3-(formylamino)-2-hydroxybenzamide (226551-21-9), (3.32) 2-{2-[(2,5-dimethylphenoxy)methyl]phenyl}-2-methoxy-N-methylacetamide (173662-97-0) and (3.33) (2R)-2-{2-[(2,5-dimethylphenoxy)methyl]phenyl}-2-methoxy-N-methylacetamide (394657-24-0).

(4) Inhibitors of the mitosis and cell division, for example (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolide (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluorophenyl)[1,2,4]triazolo[1,5-a]pyrimidine (214706-53-3) and (4.14) 3-chloro-5-(6-chloropyridin-3-yl)-6-methyl-4-(2,4,6-trifluorophenyl)pyridazine (1002756-87-7).

(5) Compounds capable to have a multisite action, like for example (5.1) bordeaux mixture (8011-63-0), (5.2) captafol (2425-06-1), (5.3) captan (133-06-2) (WO 02/12172), (5.4) chlorothalonil (1897-45-6), (5.5) copper hydroxide (20427-59-2), (5.6) copper naphthenate (1338-02-9), (5.7) copper oxide (1317-39-1), (5.8) copper oxychloride (1332-40-7), (5.9) copper (2+) sulfate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (8018-01-7), (5.24) maneb (12427-38-2), (5.25) metiram (9006-42-2), (5.26) metiram zinc (9006-42-2), (5.27) oxinecopper (10380-28-5), (5.28) propamidine (104-32-5), (5.29) propineb (12071-83-9), (5.30) sulphur and sulphur preparations including calcium polysulphide (7704-34-9), (5.31) thiram (137-26-8), (5.32) tolylfluanid (731-27-1), (5.33) zineb (12122-67-7) and (5.34) ziram (137-30-4).

(6) Compounds capable to induce a host defence, for example (6.1) acibenzolar-5-methyl (135158-54-2), (6.2) isotianil (224049-04-1), (6.3) probenazole (27605-76-1) and (6.4) tiadinil (223580-51-6).

(7) Inhibitors of the amino acid and/or protein biosynthesis, for example (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0) and (7.8) 3-(5-fluoro-3,3,4,4-tetramethyl-3,4-dihydroisoquinolin-1-yl)quinoline (861647-32-7) (WO2005070917).

(8) Inhibitors of the ATP production, for example (8.1) fentin acetate (900-95-8), (8.2) fentin chloride (639-58-7), (8.3) fentin hydroxide (76-87-9) and (8.4) silthiofam (175217-20-6).

(9) Inhibitors of the cell wall synthesis, for example (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8) and (9.9) valifenalate (283159-94-4; 283159-90-0).

(10) Inhibitors of the lipid and membrane synthesis, for example (10.1) biphenyl (92-52-4), (10.2) chloroneb (2675-77-6), (10.3) dicloran (99-30-9), (10.4) edifenphos (17109-49-8), (10.5) etridiazole (2593-15-9), (10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0) and (10.15) tolclofos-methyl (57018-04-9).

(11) Inhibitors of the melanine biosynthesis, for example (11.1) carpropamid (104030-54-8), (11.2) diclocymet (139920-32-4), (11.3) fenoxanil (115852-48-7), (11.4) phthalide (27355-22-2), (11.5) pyroquilon (57369-32-1), (11.6) tricyclazole (41814-78-2) and (11.7) 2,2,2-trifluoroethyl {3-methyl-1-[(4-methylbenzoyl)amino]butan-2-yl}carbamate (851524-22-6) (WO2005042474).

(12) Inhibitors of the nucleic acid synthesis, for example (12.1) benalaxyl (71626-11-4), (12.2) benalaxyl-M (kiralaxyl) (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazol (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3) and (12.13) oxolinic acid (14698-29-4).

(13) Inhibitors of the signal transduction, for example (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7) and (13.7) vinclozolin (50471-44-8).

(14) Compounds capable to act as an uncoupler, for example (14.1) binapacryl (485-31-4), (14.2) dinocap (131-72-6), (14.3) ferimzone (89269-64-7), (14.4) fluazinam (79622-59-6) and (14.5) meptyldinocap (131-72-6).

(15) Further compounds, for example (15.1) benthiazole (21564-17-0), (15.2) bethoxazin (163269-30-5), (15.3) capsimycin (70694-08-5), (15.4) carvone (99-49-0), (15.5) chinomethionat (2439-01-2), (15.6) pyrifenone (chlazafenone) (688046-61-9), (15.7) cufraneb (11096-18-7), (15.8) cyflufenamid (180409-60-3), (15.9) cymoxanil (57966-95-7), (15.10) cyprosulfamide (221667-31-8), (15.11) dazomet (533-74-4), (15.12) debacarb (62732-91-6), (15.13) dichlorophen (97-23-4), (15.14) diclomezine (62865-

36-5), (15.15) difenzoquat (49866-87-7), (15.16) difenzoquat methylsulphate (43222-48-6), (15.17) diphenylamine (122-39-4), (15.18) ecomate, (15.19) fenpyrazamine (473798-59-3), (15.20) flumetover (154025-04-4), (15.21) fluoroimide (41205-21-4), (15.22) flusulfamide (106917-52-6), (15.23) flutianil (304900-25-2), (15.24) fosetyl-aluminium (39148-24-8), (15.25) fosetyl-calcium, (15.26) fosetyl-sodium (39148-16-8), (15.27) hexachlorobenzene (118-74-1), (15.28) irumamycin (81604-73-1), (15.29) methasulfocarb (66952-49-6), (15.30) methyl isothiocyanate (556-61-6), (15.31) metrafenone (220899-03-6), (15.32) mildiomycin (67527-71-3), (15.33) natamycin (7681-93-8), (15.34) nickel dimethyldithiocarbamate (15521-65-0), (15.35) nitrothal-isopropyl (10552-74-6), (15.36) octhilinone (26530-20-1), (15.37) oxamocarb (917242-12-7), (15.38) oxyfenthiin (34407-87-9), (15.39) pentachlorophenol and salts (87-86-5), (15.40) phenothrin, (15.41) phosphorous acid and its salts (13598-36-2), (15.42) propamocarb-fosetylate, (15.43) propanosine-sodium (88498-02-6), (15.44) proquinazid (189278-12-4), (15.45) pyrimorph (868390-90-3), (15.45e) (2E)-3-(4-tert-butylphenyl)-3-(2-chloropyridin-4-yl)-1-(morpholin-4-yl)prop-2-en-1-one (1231776-28-5), (15.45z) (2Z)-3-(4-tert-butylphenyl)-3-(2-chloropyridin-4-yl)-1-(morpholin-4-yl)prop-2-en-1-one (1231776-29-6), (15.46) pyrroInitrine (1018-71-9) (EP-A 1 559 320), (15.47) tebufloquin (376645-78-2), (15.48) tecloftalam (76280-91-6), (15.49) tolnifanide (304911-98-6), (15.50) triazoxide (72459-58-6), (15.51) trichlamide (70193-21-4), (15.52) zarilamid (84527-51-5), (15.53) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate (517875-34-2) (WO2003035617), (15.54) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-79-6) (WO 2008013622), (15.55) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-80-9) (WO 2008013622), (15.56) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003318-67-9) (WO 2008013622), (15.57) 1-(4-methoxyphenoxy)-3,3-dimethylbutan-2-yl 1H-imidazole-1-carboxylate (111227-17-9), (15.58) 2,3,5,6-tetrachloro-4-(methylsulfonyl)pyridine (13108-52-6), (15.59) 2,3-dibutyl-6-chlorothieno[2,3-d]pyrimidin-4(3H)-one (221451-58-7), (15.60) 2,6-dimethyl-1H,5H-[1,4]dithiino[2,3-c: 5,6-c']dipyrrole-1,3,5,7(2H,6H)-tetrone, (15.61) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone (1003316-53-7) (WO 2008013622), (15.62) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone (1003316-54-8) (WO 2008013622), (15.63) 2-[5-methyl-3-(trifluoromethyl)-1H-pyrazol-1-yl]-1-{4-[4-(5-phenyl-4,5-dihydro-1,2-oxazol-3-yl]-1,3-thiazol-2-yl}piperidin-1-yl]ethanone (1003316-51-5) (WO 2008013622), (15.64) 2-butoxy-6-iodo-3-propyl-4H-chromen-4-one, (15.65) 2-chloro-5-[2-chloro-1-(2,6-difluoro-4-methoxyphenyl)-4-methyl-1H-imidazol-5-yl]pyridine, (15.66) 2-phenylphenol and salts (90-43-7), (15.67) 3-(4,4,5-trifluoro-3,3-dimethyl-3,4-dihydroisoquinolin-1-yl)quinoline (861647-85-0) (WO2005070917), (15.68) 3,4,5-trichloropyridine-2,6-dicarbonitrile (17824-85-0), (15.69) 3-[5-(4-chlorophenyl)-2,3-dimethyl-1,2-oxazolidin-3-yl]pyridine, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulfonohydrazide (134-31-6), (15.74) 5-fluoro-2-[(4-fluorobenzyl)oxy]pyrimidin-4-amine (1174376-11-4) (WO2009094442), (15.75) 5-fluoro-2-[(4-methylbenzyl)oxy]pyrimidin-4-amine (1174376-25-0) (WO2009094442), (15.76) 5-methyl-6-octyl[1,2,4]triazolo[1,5-a]pyrimidin-7-amine, (15.77) ethyl (2Z)-3-amino-2-cyano-3-phenylprop-2-enoate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloropyridine-3-carboxamide, (15.82) N-[1-(5-bromo-3-chloropyridin-2-yl)ethyl]-2,4-dichloropyridine-3-carboxamide, (15.83) N-[1-(5-bromo-3-chloropyridin-2-yl)ethyl]-2-fluoro-4-iodopyridine-3-carboxamide, (15.84) N-{(E)-[(cyclopropylmethoxy)imino][6-(difluoromethoxy)-2,3-difluorophenyl]methyl}-2-phenylacetamide (221201-92-9), (15.85) N-{(Z)-[(cyclopropylmethoxy)imino][6-(difluoromethoxy)-2,3-difluorophenyl]methyl}-2-phenylacetamide (221201-92-9), (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide (922514-49-6) (WO 2007014290), (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide (922514-07-6) (WO 2007014290), (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide (922514-48-5) (WO 2007014290), (15.90) pentyl {6-[({[(1-methyl-1H-tetrazol-5-yl)(phenyl)methylidene]amino}oxy)methyl]pyridin-2-yl}carbamate, (15.91) phenazine-1-carboxylic acid, (15.92) quinolin-8-ol (134-31-6), (15.93) quinolin-8-ol sulfate (2:1) (134-31-6) and (15.94) tert-butyl {6-[({[(1-methyl-1H-tetrazol-5-yl)(phenyl)methylene]amino}oxy)methyl]pyridin-2-yl}carbamate.

(16) Further compounds, for example (16.1) 1-methyl-3-(trifluoromethyl)-N-[2'-(trifluoromethyl)biphenyl-2-yl]-1H-pyrazole-4-carboxamide, (16.2) N-(4'-chlorobiphenyl-2-yl)-3-(difluoromethyl)-1-methyl-1H-pyrazole-4-carboxamide, (16.3) N-(2',4'-dichlorobiphenyl-2-yl)-3-(difluoromethyl)-1-methyl-1H-pyrazole-4-carboxamide, (16.4) 3-(difluoromethyl)-1-methyl-N-[4'-(trifluoromethyl)biphenyl-2-yl]-1H-pyrazole-4-carboxamide, (16.5) N-(2',5'-difluorobiphenyl-2-yl)-1-methyl-3-(trifluoromethyl)-1H-pyrazole-4-carboxamide, (16.6) 3-(difluoromethyl)-1-methyl-N-[4'-(prop-1-yn-1-yl)biphenyl-2-yl]-1H-pyrazole-4-carboxamide (known from WO 2004/058723), (16.7) 5-fluoro-1,3-dimethyl-N-[4'-(prop-1-yn-1-yl)biphenyl-2-yl]-1H-pyrazole-4-carboxamide (known from WO 2004/058723), (16.8) 2-chloro-N-[4'-(prop-1-yn-1-yl)biphenyl-2-yl]pyridine-3-carboxamide (known from WO 2004/058723), (16.9) 3-(difluoromethyl)-N-[4'-(3,3-dimethylbut-1-yn-1-yl)biphenyl-2-yl]-1-methyl-1H-pyrazole-4-carboxamide (known from WO 2004/058723), (16.10) N-[4'-(3,3-dimethylbut-1-yn-1-yl)biphenyl-2-yl]-5-fluoro-1,3-dimethyl-1H-pyrazole-4-carboxamide (known from WO 2004/058723), (16.11) 3-(difluoromethyl)-N-(4'-ethynylbiphenyl-2-yl)-1-methyl-1H-pyrazole-4-carboxamide (known from WO 2004/

058723), (16.12) N-(4'-ethynylbiphenyl-2-yl)-5-fluoro-1,3-dimethyl-1H-pyrazole-4-carboxamide (known from WO 2004/058723), (16.13) 2-chloro-N-(4'-ethynylbiphenyl-2-yl)pyridine-3-carboxamide (known from WO 2004/058723), (16.14) 2-chloro-N-[4'-(3,3-dimethylbut-1-yn-1-yl)biphenyl-2-yl]pyridine-3-carboxamide (known from WO 2004/058723), (16.15) 4-(difluoromethyl)-2-methyl-N-[4'-(trifluoromethyl)biphenyl-2-yl]-1,3-thiazole-5-carboxamide (known from WO 2004/058723), (16.16) 5-fluoro-N-[4'-(3-hydroxy-3-methylbut-1-yn-1-yl)biphenyl-2-yl]-1,3-dimethyl-1H-pyrazole-4-carboxamide (known from WO 2004/058723), (16.17) 2-chloro-N-[4'-(3-hydroxy-3-methylbut-1-yn-1-yl)biphenyl-2-yl]pyridine-3-carboxamide (known from WO 2004/058723), (16.18) 3-(difluoromethyl)-N-[4'-(3-methoxy-3-methylbut-1-yn-1-yl)biphenyl-2-yl]-1-methyl-1H-pyrazole-4-carboxamide (known from WO 2004/058723), (16.19) 5-fluoro-N-[4'-(3-methoxy-3-methylbut-1-yn-1-yl)biphenyl-2-yl]-1,3-dimethyl-1H-pyrazole-4-carboxamide (known from WO 2004/058723), (16.20) 2-chloro-N-[4'-(3-methoxy-3-methylbut-1-yn-1-yl)biphenyl-2-yl]pyridine-3-carboxamide (known from WO 2004/058723), (16.21) (5-bromo-2-methoxy-4-methylpyridin-3-yl)(2,3,4-trimethoxy-6-methylphenyl)methanone (known from EP-A 1 559 320), (16.22) N-[2-(4-{[3-(4-chlorophenyl)prop-2-yn-1-yl]oxy}-3-methoxyphenyl)ethyl]-N2-(methylsulfonyl)valinamide (220706-93-4), (16.23) 4-oxo-4-[(2-phenylethyl)amino]butanoic acid and (16.24) but-3-yn-1-yl {6-[({[(Z)-(1-methyl-1H-tetrazol-5-yl)(phenyl)methylene]amino}oxy)methyl]pyridin-2-yl}carbamate.

All named combination partners of the classes (1) to (16), as well as the SDHIs, in particular bixafen, penflufen and fluopyram of the present invention can, if their functional groups enable this, optionally form salts with suitable bases or acids.

In one embodiment a composition comprising the SDHIs, in particular bixafen, penflufen or fluopyram according to the present invention may comprise one or more additional fungicides which may be selected from the group consisting of:

(1) Inhibitors of the ergosterol biosynthesis, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-[1-(4-methoxyphenoxy)-3,3-dimethylbutan-2-yl]1H-imidazole-1-carbothioate and (2) inhibitors of the respiratory chain at complex I or II, for example (2.1) bixafen (581809-46-3), (2.2) boscalid (188425-85-6), (2.3) carboxin (5234-68-4), (2.4) diflumetorim (130339-07-0), (2.5) fenfuram (24691-80-3), (2.6) fluopyram (658066-35-4), (2.7) flutolanil (66332-96-5), (2.8) fluxapyroxad (907204-31-3), (2.9) furametpyr (123572-88-3), (2.10) furmecyclox (60568-05-0), (2.11) isopyrazam (mixture of syn-epimeric racemate 1RS,4SR,9RS and anti-epimeric racemate 1RS,4SR,9SR) (881685-58-1), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil (55814-41-0), (2.19) oxycarboxin (5259-88-1), (2.20) penflufen (494793-67-8), (2.21) penthiopyrad (183675-82-3), (2.22) sedaxane (874967-67-6), (2.23) thifluzamide (130000-40-7), (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide (1092400-95-7) (WO 2008148570), (2.28) 5,8-difluoro-N-[2-(2-fluoro-4-{[4-(trifluoromethyl)pyridin-2-yl]oxy}phenyl)ethyl]quinazolin-4-amine (1210070-84-0) (WO2010025451), (2.29) N-[9-(dichloromethylene)-1,2,3,4-tetrahydro-1,4-methanonaphthalen-5-yl]-3-(difluoroethyl)-1-methyl-1H-pyrazole-4-carboxamide, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) inhibitors of the respiratory chain at complex III, for example (3.1) ametoctradin (865318-97-4), (3.2) amisulbrom (348635-87-0), (3.3) azoxystrobin (131860-33-8), (3.4) cyazofamid (120116-88-3), (3.5) coumethoxystrobin (850881-30-0), (3.6) coumoxystrobin (850881-70-8), (3.7) dimoxystrobin (141600-52-4), (3.8) enestroburin (238410-11-2) (WO 2004/058723), (3.9) famoxadone (131807-57-3) (WO 2004/058723), (3.10) fenamidone (161326-34-7) (WO 2004/058723), (3.11) fenoxystrobin (918162-02-4), (3.12) fluoxastrobin (361377-29-9) (WO 2004/058723), (3.13) kresoxim-methyl (143390-89-0) (WO 2004/058723), (3.14) metominostrobin (133408-50-1) (WO 2004/058723), (3.15) orysastrobin (189892-69-1) (WO 2004/058723), (3.16) picoxystrobin (117428-22-5) (WO 2004/058723), (3.17) pyraclostrobin (175013-18-0) (WO 2004/058723), (3.18) pyrametostrobin (915410-70-7) (WO 2004/058723), (3.19) pyraoxystrobin (862588-11-2) (WO 2004/058723), (3.20) pyribencarb (799247-52-2) (WO 2004/058723), (3.21) triclopyricarb (902760-40-1), (3.22) trifloxystrobin (141517-21-7) (WO 2004/058723), (3.23) (2E)-2-(2-[6-(3-chloro-2-methylphenoxy)-5-fluoropyrimidin-4-yl]oxy 1-phenyl)-2-(methoxyimino)-N-methylethanamide (WO 2004/058723), (3.24) (2E)-2-(methoxyimino)-N-methyl-2-(2-{[({(1E)-1-[3-(trifluoromethyl)phenyl]ethylidene}amino)oxy]methyl}phenyl)ethanamide (WO 2004/058723), (3.25) (2E)-2-(methoxyimino)-N-methyl-2-{2-[(E)-({1-[3-(trifluoromethyl)phenyl]ethoxy}imino)methyl]phenyl}ethanamide (158169-73-4), (3.26) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide (119899-

14-8), (3.29) 5-methoxy-2-methyl-4-(2-{[({(1E)-1-[3-(trifluoromethyl)phenyl]ethylidene}amino)oxy]methyl}-phenyl)-2,4-dihydro-3H-1,2,4-triazol-3-one, (3.30) methyl (2E)-2-{2-[({cyclopropyl[(4-methoxyphenyl)imino] methyl}sulfanyl)methyl]phenyl}-3-methoxyprop-2-enoate (149601-03-6), (3.31) N-(3-ethyl-3,5,5-trimethylcyclohexyl)-3-(formylamino)-2-hydroxybenzamide (226551-21-9), (3.32) 2-{2-[(2,5-dimethylphenoxy)methyl]phenyl}-2-methoxy-N-methylacetamide (173662-97-0) and (3.33) (2R)-2-{2-[(2,5-dimethylphenoxy)methyl]phenyl}-2-methoxy-N-methylacetamide (394657-24-0) and

(15) Further compounds, for example benthiazole, bethoxazin, capsimycin, carvone, chinomethionat, pyriofenone (chlazafenone), cufraneb, cyflufenamid, cymoxanil, cyprosulfamide, dazomet, debacarb, dichlorophen, diclomezine, difenzoquat, difenzoquat methylsulphate, diphenylamine, ecomate, fenpyrazamine, flumetover, fluoroimide, flusulfamide, flutianil, fosetyl-aluminium, fosetyl-calcium, fosetyl-sodium, hexachlorobenzene, irumamycin, methasulfocarb, methyl isothiocyanate, metrafenone, mildiomycin, natamycin, nickel dimethyldithiocarbamate, nitrothal-isopropyl, octhilinone, oxamocarb, oxyfenthiin, pentachlorophenol and salts, phenothrin, phosphorous acid and its salts, propamocarb-fosetylate, propanosine-sodium, proquinazid, pyrimorph, (2E)-3-(4-tert-butylphenyl)-3-(2-chloropyridin-4-yl)-1-(morpholin-4-yl)prop-2-en-1-one, (2Z)-3-(4-tert-butylphenyl)-3-(2-chloropyridin-4-yl)-1-(morpholin-4-yl) prop-2-en-1-one, pyrrolnitrine, tebufloquin, tecloftalam, tolnifanide, triazoxide, trichlamide, zarilamid, (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulfonyl) pyridine, 2,3-dibutyl-6-chlorothieno[2,3-d]pyrimidin-4 (3H)-one, 2,6-dimethyl-1H,5H-[1,4]dithiino[2,3-c:5,6-c'] dipyrrole-1,3,5,7(2H,6H)-tetrone, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl) ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts, 3-(4,4,5-trifluoro-3,3-dimethyl-3,4-dihydroisoquinolin-1-yl)quinoline, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulfonohydrazide, 5-fluoro-2-[(4-fluorobenzyl)oxy]pyrimidin-4-amine, 5-fluoro-2-[(4-methylbenzyl)oxy]pyrimidin-4-amine, 5-methyl-6-octyl[1,2,4]triazolo[1,5-a]pyrimidin-7-amine, ethyl (2Z)-3-amino-2-cyano-3-phenylprop-2-enoate, N'-(4-{[3-(4-chlorobenzyl)-1,2,4-thiadiazol-5-yl]oxy}-2,5-dimethylphenyl)-N-ethyl-N-methylimidoformamide, N-(4-chlorobenzyl)-3-[3-methoxy-4-(prop-2-yn-1-yloxy)phenyl] propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)-methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N'-{4-[(3-tert-butyl-4-cyano-1,2-thiazol-5-yl)oxy]-2-chloro-5-methylphenyl}-N-ethyl-N-methylimidoformamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl)methylidene]amino}oxy)methyl]pyridin-2-yl}carbamate, phenazine-1-carboxylic acid, quinolin-8-ol, quinolin-8-ol sulfate (2:1) and tert-butyl {6-[({[(1-methyl-1H-tetrazol-5-yl)(phenyl)methylene]amino}oxy)methyl]pyridin-2-yl}carbamate.

In one embodiment a composition comprising the SDHIs, in particular bixafen, penflufen or fluopyram according to the present invention may comprise one or more additional fungicides which may be selected from the group consisting of tebuconazole, prothioconazole, epoxiconazole, ipconazole, fosetyl-aluminium, fosetyl-calcium, fosetyl-sodium, phosphorous acid and its salts, propamocarb-fosetylate, trifloxystrobin.

In one embodiment a composition comprising bixafen, penflufen or fluopyram according to the present invention may comprise one or more additional fungicides which may be selected from the group consisting of tebuconazole, prothioconazole, epoxiconazole, ipconazole, fosetyl-aluminium, fosetyl-calcium, fosetyl-sodium, phosphorous acid and its salts, propamocarb-fosetylate, trifloxystrobin.

In one embodiment a composition comprising bixafen according to the present invention may comprise one or more additional fungicides which may be selected from the group consisting of tebuconazole, prothioconazole, epoxiconazole, ipconazole, fosetyl-aluminium, fosetyl-calcium, fosetyl-sodium, phosphorous acid and its salts, propamocarb-fosetylate, trifloxystrobin.

In one embodiment a composition comprising penflufen according to the present invention may comprise one or more additional fungicides which may be selected from the group consisting of tebuconazole, prothioconazole, epoxiconazole, ipconazole, fosetyl-aluminium, fosetyl-calcium, fosetyl-sodium, phosphorous acid and its salts, propamocarb-fosetylate, trifloxystrobin.

In one embodiment a composition comprising fluopyram according to the present invention may comprise one or more additional fungicides which may be selected from the group consisting of tebuconazole, prothioconazole, epoxiconazole, ipconazole, fosetyl-aluminium, fosetyl-calcium, fosetyl-sodium, phosphorous acid and its salts, propamocarb-fosetylate, trifloxystrobin.

In one embodiment a composition comprising fluopyram according to the present invention may comprise one or more additional fungicides which may be selected from the group consisting of tebuconazole, prothioconazole, epoxiconazole, ipconazole, fosetyl-aluminium, fosetyl-calcium, fosetyl-sodium, phosphorous acid and its salts, propamocarb-fosetylate, trifloxystrobin.

In one embodiment a composition comprising fluopyram according to the present invention may comprise tebuconazole.

In one embodiment the active ingredient of a composition consists out of one SDHI as defined above.

In one embodiment the active ingredient of a composition consists out of bixafen.

In one embodiment the active ingredient of a composition consists out of penflufen.

In one embodiment the active ingredient of a composition consists out of fluopyram.

In one embodiment the active ingredients of a composition consists out of fluopyram and tebuconazole.

Compositions

The fungicidal compositions of the present invention comprising the SDHIs may further comprise at least one other additional component such as auxiliaries, solvents, carriers or supports, filler, surfactants or extenders, all being agriculturally acceptable.

According to the invention the term "support" or "carrier" is to be understood as meaning a natural or synthetic, organic or inorganic substance which is mixed or combined with the active compounds for better applicability, in particular for application to plants or plant parts or seeds. The support or carrier, which may be solid or liquid, is generally inert and should be suitable for use in agriculture. Suitable solid or liquid carriers/supports include for example ammonium salts and natural ground minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral oils and vegetable oils, and also derivatives thereof. It is also possible to use mixtures of such supports or carriers. Solid supports/carriers suitable for granules are: for example crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks. Suitable liquefied gaseous extenders or carriers are liquids which are gaseous at ambient temperature and under atmospheric pressure, for example aerosol propellants, such as butane, propane, nitrogen and carbon dioxide. Tackifiers, such as carboxymethylcellulose and natural and synthetic polymers in the form of powders, granules and latices, such as gum arabic, polyvinyl alcohol, polyvinyl acetate, or else natural phospholipids, such as cephalins and lecithins and synthetic phospholipids can be used in the formulations. Other possible additives are mineral and vegetable oils and waxes, optionally modified. If the extender used is water, it is also possible for example, to use organic solvents as auxiliary solvents. Suitable liquid solvents are essentially: aromatic compounds, such as xylene, toluene or alkylnaphthalenes, chlorinated aromatic compounds or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulphoxide, and also water.

In the present specification, the term "surfactant" comprises an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be comprised between 5% and 40% by weight of the composition.

Additional components may also be included, e.g. protective colloids, adhesives, thickeners, thixotropic agents, penetration agents, stabilisers, sequestering agents. More generally, the active materials can be combined with any solid or liquid additive, which complies with the usual formulation techniques.

It is further possible to use colourants such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

In general, the compositions according to the invention may contain from 0.05 to 99% (by weight) of active material, preferably 0.1 to 95% by weight, more preferably 1 to 90% by weight, most preferably 10 to 70% by weight.

Compositions according to the present invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before they are applied to the crop.

In one embodiment, the SDHIs, are applied by dipping, spraying, atomizing, irrigating, evaporating, painting, spreading-on, watering (drenching), drip irrigating, chemigating (i.e. by addition of the active ingredients to the irrigation water, injection and in hydroponic/mineral systems) or injecting the plants, plant parts, plants growing from seedlings, root-stocks, grafts and cuttings or the soil to be treated.

In one embodiment, the SDHIs, are applied by dipping, spraying, atomizing, irrigating, evaporating, painting, spreading-on, watering (drenching), drip irrigating, chemigating or injecting seedlings, root-stocks, grafts and cuttings, stems, shoots, trunks, and leaves to be treated.

In one embodiment, bixafen, penflufen and fluopyram are applied by dipping, spraying, atomizing, irrigating, evaporating, painting, spreading-on, watering (drenching), drip irrigating, chemigating or injecting seedlings, root-stocks, grafts and cuttings, the stems, shoots, trunks, and leaves to be treated.

In one embodiment, fluopyram is applied by dipping, spraying, atomizing, irrigating, evaporating, painting, spreading-on, watering (drenching), drip irrigating, chemigating or injecting seedlings, root-stocks, grafts and cuttings, stems, shoots, trunks, and leaves to be treated.

In one embodiment, bixafen, penflufen and fluopyram are applied by dipping, spraying, irrigating, painting, spreading-on, watering (drenching), drip irrigating, chemigating or injecting seedlings, root-stocks, grafts and cuttings, stems, shoots, trunks, and leaves to be treated.

In one embodiment, fluopyram is applied by dipping, spraying, irrigating, painting, spreading-on, watering (drenching), drip irrigating, chemigating or injecting seedlings, root-stocks, grafts and cuttings, stems, shoots, trunks, and leaves to be treated.

The use of the succinate dehydrogenase inhibitors envisaged in accordance with the invention, preferably of fluopyram, bixafen or penflufen are effected preferably with an application rate between 0.01 and 3 kg/ha of active ingredient, more preferably between 0.05 and 2 kg/ha, even more preferably between 0.1 and 1 kg/ha, much more preferably between 0.1 and 0.5 kg/ha.

In one embodiment the application rate is 0.05 to 0.5 kg/ha.
Formulations

Depending on their particular physical and/or chemical properties, fluopyram, bixafen or penflufen can be converted in accordance with the invention to the customary formulations, such as solutions, emulsions, suspensions, powders, foams, pastes, granules, aerosols and microencapsulations in polymeric substances and in coating materials for seed, and also ULV cool and warm fogging formulations.

The formulations contain generally between 0.01 and 95 percent by weight of active ingredient, preferably between 0.05 and 90%, more preferably between 0.1 and 80%.

These formulations are produced in a known manner, for example by mixing the active ingredients with extenders, i.e. liquid solvents, liquefied gases under pressure and/or solid carriers, optionally using surfactants, i.e. emulsifiers and/or dispersants, and/or foam formers. If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are understood to mean those liquids which are gaseous at standard temperature and under standard pressure, for example aerosol propellants such as halohydrocarbons, or else butane, propane, nitrogen and carbon dioxide. Useful solid carriers are: for example natural rock flours such as kaolins, clays, talc, chalk, quartz, attapulgite, montmorillonite or diatomaceous earth, and synthetic rock flours such as finely divided silica, alumina and silicates. Useful solid carriers for granules are: for example crushed and fractionated natural rocks such as calcite, pumice, marble, sepiolite, dolomite, and synthetic granules of inorganic and organic flours, and also granules of organic material such as sawdust, coconut shells, maize cobs and tobacco stalks. Useful emulsifiers and/or foam generators are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Useful dispersants include: for example lignosulphite waste liquors and methylcellulose.

In the formulations it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral and vegetable oils.

It is possible to use colorants such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

One of the advantages of the present invention is that, owing to the particular systemic properties of fluopyram, bixafen or penflufen, the treatment of the plants, plant parts as for example leaves, stems, trunks and shoots, and plants grown from seedlings, root stocks, grafts and cuttings with fluopyram, bixafen or penflufen enables not only the control of wood diseases on the plant itself, but also on the plant parts which originate therefrom after plant growth. In this way, the immediate treatment of the crop before or at the time of transplanting, or after can be dispensed.
GMOs Particular preference is given in accordance with the invention to treating plants of the plant cultivars which are each commercially available or in use. Plant cultivars are understood to mean plants which have new properties ("traits") and which have been obtained by conventional breeding, by mutagenesis or with the aid of recombinant DNA techniques. Crop plants may accordingly be plants which can be obtained by conventional breeding and optimization methods or by biotechnology and genetic engineering methods or combinations of these methods, including the transgenic plants and including the plant varieties which can and cannot be protected by plant variety rights.

The method according to the invention can thus also be used for the treatment of genetically modified organisms (GMOs), for example plants or seeds. Genetically modified plants (or transgenic plants) are plants in which a heterologous gene has been integrated stably into the genome. The term "heterologous gene" means essentially a gene which is provided or assembled outside the plant and which, on introduction into the cell nucleus genome, imparts new or improved agronomic or other properties to the chloroplast genome or the mitochondrial genome of the transformed plant by virtue of it expressing a protein or polypeptide of interest or by virtue of another gene which is present in the plant, or other genes which are present in the plant, being downregulated or silenced (for example by means of antisense technology, co-suppression technology or RNAi technology [RNA interference]). A heterologous gene present in the genome is likewise referred to as a transgene. A transgene which is defined by its specific presence in the plant genome is referred to as a transformation or transgenic event.

Plants and plant cultivars which are preferably treated according to the invention include all plants which have genetic material which imparts particularly advantageous, useful traits to these plants (whether obtained by breeding and/or biotechnological means).

Plants and plant cultivars which may also be treated in according to invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients or shade avoidance.

Plants and plant cultivars which may also be treated according to the invention are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may also be treated according to the invention are hybrid plants that already express the characteristic of heterosis or hybrid vigour which generally results in higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in maize) be produced by detasseling, i.e. the mechanical removal of the male reproductive organs (or male flowers), but, more typically, male sterility is the result of genetic determinants in the plant genome. In that case, and especially when seed is the desired product to be harvested from the hybrid plants, it is typically useful to ensure that male fertility in hybrid plants that contain the genetic determinants responsible for the male sterility is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmatic male sterility (CMS) were for instance described in *Brassica* species (WO 1992/005251, WO 1995/009910, WO 1998/27806, WO 2005/002324, WO 2006/021972 and U.S. Pat. No. 6,229,072). However, genetic determinants for male sterility can also be located in the nuclear genome. Male-sterile plants can also be obtained by plant biotechnology methods such as genetic engineering. A particularly useful means of obtaining male-sterile plants is described in WO 89/10396, in which, for example, a ribonuclease such as barnase is selectively expressed in the tapetum cells in the stamens. Fertility can then be restored by expression in the tapetum cells of a ribonuclease inhibitor such as barstar (e.g. WO 1991/002069).

Plants or plant cultivars (obtained by plant biotechnology methods such as genetic engineering) which may likewise be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a petunia EPSPS (Shah et al., Science (1986), 233, 478-481), a tomato EPSPS (Gasser et al., J. Biol. Chem. (1988), 263, 4280-4289) or an *Eleusine* EPSPS (WO 2001/66704). It can also be a mutated EPSPS, as described, for example, in EP-A 0837944, WO 2000/066746, WO 2000/066747 or WO 2002/026995. Glyphosate-tolerant plants can also be obtained by expressing a gene that encodes a glyphosate oxidoreductase enzyme as described in U.S. Pat. No. 5,776,760 and U.S. Pat. No. 5,463,175. Glyphosate-tolerant plants can also be obtained by expressing a gene that encodes a glyphosate acetyl transferase enzyme as described, for example, in WO 2002/036782, WO 2003/092360, WO 2005/012515 and WO 2007/024782. Glyphosate-tolerant plants can also be obtained by selecting plants containing naturally occurring mutations of the above-mentioned genes as described, for example, in WO 2001/024615 or WO 2003/013226.

Other herbicide-resistant plants are for example plants that have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species). Plants expressing an exogenous phosphinothricin acetyltransferase are for example described in U.S. Pat. No. 5,561,236; U.S. Pat. No. 5,648,477; U.S. Pat. No. 5,646,024; U.S. Pat. No. 5,273,894; U.S. Pat. No. 5,637,489; U.S. Pat. No. 5,276,268; U.S. Pat. No. 5,739,082; U.S. Pat. No. 5,908,810 and U.S. Pat. No. 7,112,665.

Further herbicide-tolerant plants are also plants that have been made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is transformed into homogentisate. Plants tolerant to HPPD-inhibitors can be transformed with a gene encoding a naturally occurring resistant HPPD enzyme, or a gene encoding a mutated HPPD enzyme according to WO 1996/038567, WO 1999/024585 and WO 1999/024586. Tolerance to HPPD inhibitors can also be obtained by transforming plants with genes encoding certain enzymes enabling the formation of homogentisate despite the inhibition of the native HPPD enzyme by the HPPD inhibitor. Such plants and genes are described in WO 1999/034008 and WO 2002/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928.

Further herbicide-resistant plants are plants that have been made tolerant to acetolactate synthase (ALS) inhibitors. Known ALS-inhibitors include, for example, sulphonylurea, imidazolinone, triazolopyrimidines, pyrimidinyloxy(thio) benzoates, and/or sulphonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright, Weed Science (2002), 50, 700-712, but also in U.S. Pat. No. 5,605,011, U.S. Pat. No. 5,378,824, U.S. Pat. No. 5,141,870 and U.S. Pat. No. 5,013,659. The production of sulphonylurea-tolerant plants and imidazolinone-tolerant plants is described in U.S. Pat. No. 5,605,011; U.S. Pat. No. 5,013,659; U.S. Pat. No. 5,141,870; U.S. Pat. No. 5,767,361; U.S. Pat. No. 5,731,180; U.S. Pat. No. 5,304,732; U.S. Pat. No. 4,761,373; U.S. Pat. No. 5,331,107; U.S. Pat. No. 5,928,937; and U.S. Pat. No. 5,378,824; and international publication WO 1996/033270. Other imidazolinone-tolerant plants are also described in for example WO 2004/040012, WO 2004/106529, WO 2005/020673, WO 2005/093093, WO 2006/007373, WO 2006/015376, WO 2006/024351 and WO 2006/060634. Further sulphonylurea- and imidazolinone-tolerant plants are also described in for example WO 2007/024782.

Other plants tolerant to imidazolinone and/or sulphonylurea can be obtained by induced mutagenesis, selection in cell cultures in the presence of the herbicide or by mutation breeding as described for example for soya beans in U.S. Pat. No. 5,084,082, for rice in WO 1997/41218, for sugar beet in U.S. Pat. No. 5,773,702 and WO 1999/057965, for lettuce in U.S. Pat. No. 5,198,599 or for sunflower in WO 2001/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

The term "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al., Microbiology and Molecular Biology Reviews (1998), 62, 807-813, updated by Crickmore et al. (2005) in the *Bacillus thuringiensis* toxin nomenclature, online at:
   http://www.lifesci.sussex.ac.uk/Home/Neil_Crickmore/Bt/), or insecticidal portions thereof, e.g. proteins of the Cry protein classes Cry1Ab, Cry1Ac, Cry1F, Cry2Ab, Cry3Ae or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins (Moellenbeck et al., Nat. Biotechnol. (2001), 19, 668-72; Schnepf et al., Applied Environm. Microb. (2006), 71, 1765-1774); or 3) a hybrid insecticidal protein comprising parts of two different insecticidal crystal proteins from *Bacillus thuringiensis*, such as a hybrid of the proteins of 1) above or a hybrid of the proteins of 2) above, e.g. the Cry1A.105 protein produced by maize event MON98034 (WO 2007/027777); or 4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb 1 protein in maize events MON863 or MON88017, or the Cry3A protein in maize event MIR604; or 5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/home/Neil_Crickmore/Bt/vip.html, e.g. proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 1994/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT102.

Of course, insect-resistant transgenic plants, as used herein, also include any plant comprising a combination of genes encoding the proteins of any one of the abovementioned classes 1 to 8. In one embodiment, an insect-resistant plant contains more than one transgene encoding a protein of any one of the abovementioned classes 1 to 8, to expand the range of target insect species affected or to delay insect resistance development to the plants, by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include:

a. plants which contain a transgene capable of reducing the expression and/or the activity of the poly(ADP-ribose) polymerase (PARP) gene in the plant cells or plants as described in WO 2000/004173 or EP 04077984.5 or EP 06009836.5;
b. plants which contain a stress tolerance-enhancing transgene capable of reducing the expression and/or the activity of the PARG encoding genes of the plants or plant cells as described, for example, in WO 2004/090140;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase as described, for example, in EP 04077624.7 or WO 2006/133827 or PCT/EP07/002,433.

Plants or plant cultivars (obtained by plant biotechnology methods such as genetic engineering) which may also be treated according to the invention show altered quantity, quality and/or storage stability of the harvested product and/or altered properties of specific ingredients of the harvested product such as:

1) transgenic plants which synthesize a modified starch, which in its physicochemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesized starch in wild type plant cells or plants, so that this modified starch is better suited for special applications. Said transgenic plants synthesizing a modified starch are described, for example, in EP 0571427, WO 1995/004826, EP 0719338, WO 1996/15248, WO 1996/19581, WO 1996/27674, WO 1997/11188, WO 1997/26362, WO 1997/32985, WO 1997/42328, WO 1997/44472, WO 1997/45545, WO 1998/27212, WO 1998/40503, WO 99/58688, WO 1999/58690, WO 1999/58654, WO 2000/008184, WO 2000/008185, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 1995/26407, WO 1996/34968, WO 1998/20145, WO 1999/12950, WO 1999/66050, WO 1999/53072, U.S. Pat. No. 6,734,341, WO 2000/11192, WO 1998/22604, WO 1998/32326, WO 2001/98509, WO 2001/98509, WO 2005/002359, U.S. Pat. No. 5,824,790, U.S. Pat. No. 6,013,861, WO 1994/004693, WO 1994/009144, WO 1994/11520, WO 1995/35026 and WO 1997/20936.

2) transgenic plants which synthesize non-starch carbohydrate polymers or which synthesize non-starch carbohydrate polymers with altered properties in comparison to wild type plants without genetic modification. Examples are plants producing polyfructose, especially of the inulin and levan type, as described in EP 0663956, WO 1996/001904, WO 1996/021023, WO 1998/039460 and WO 1999/024593, plants producing alpha-1,4-glucans, as described in WO 1995/031553, US 2002/031826, U.S. Pat. No. 6,284,479, U.S. Pat. No. 5,712,107, WO 1997/047806, WO 1997/047807, WO 1997/047808 and WO 2000/14249, plants producing alpha-1,6-branched alpha-1,4-glucans, as described in WO 2000/73422, and plants producing alternan, as described in WO 2000/047727, EP 06077301.7, U.S. Pat. No. 5,908,975 and EP 0728213.

3) transgenic plants which produce hyaluronan, as for example described in WO 2006/032538, WO 2007/039314, WO 2007/039315, WO 2007/039316, JP 2006/304779 and WO 2005/012529.

Plants or plant cultivars (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:

a) plants, such as cotton plants, containing an altered form of cellulose synthase genes as described in WO 1998/000549,
b) plants, such as cotton plants, containing an altered form of rsw2 or rsw3 homologous nucleic acids as described in WO 2004/053219;
c) plants, such as cotton plants, with increased expression of sucrose phosphate synthase as described in WO 2001/017333;
d) plants, such as cotton plants, with increased expression of sucrose synthase as described in WO 02/45485;

e) plants, such as cotton plants, wherein the timing of the plasmodesmatal gating at the basis of the fibre cell is altered, for example through downregulation of fibre-selective β-1,3-glucanase as described in WO 2005/017157;
f) plants, such as cotton plants, having fibres with altered reactivity, e.g. through the expression of the N-acetylglucosaminetransferase gene including nodC and chitin synthase genes as described in WO 2006/136351.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:
a) plants, such as oilseed rape plants, producing oil having a high oleic acid content, as described, for example, in U.S. Pat. No. 5,969,169, U.S. Pat. No. 5,840,946 or U.S. Pat. No. 6,323,392 or U.S. Pat. No. 6,063,947;
b) plants, such as oilseed rape plants, producing oil having a low linolenic acid content, as described in U.S. Pat. No. 6,270,828, U.S. Pat. No. 6,169,190 or U.S. Pat. No. 5,965,755.
c) plants, such as oilseed rape plants, producing oil having a low level of saturated fatty acids, as described, for example, in U.S. Pat. No. 5,434,283.

Examples of herbicide-tolerant plants which may be mentioned are varieties, which are sold under the following trade names: Roundup Ready® (tolerance to glyphosate), Liberty Link® (tolerance to phosphinotricin), IMI® (tolerance to imidazolinones) and SCS® (tolerance to sulphonylureas). Herbicide-resistant plants (plants bred in a conventional manner for herbicide tolerance) which may be mentioned include the varieties sold under the Clearfield® name.

Particularly useful transgenic plants which may be treated according to the invention are plants containing transformation events, or a combination of transformation events, that are listed for example in the databases from various national or regional regulatory agencies (see for example http://gmoinfo.jrc.it/gmp_browse.aspx and http://www.agbios.com/dbase.php).

The example which follows serves to illustrate the invention, but without restricting it.

EXAMPLES

Wood Diseases/Grapes

The following examples illustrate the efficacy compounds with mode of action SDHIs for the control of wood diseases developing in grape plants or plant parts.

This test is carried out on representative fungi found in grape plants showing "Esca" Symptoms

| Fungi community of Esca symptoms* | Disease name | Presence in infected plants* |
|---|---|---|
| *Phaemoniella chlamydospora* | Esca | 84% |
| *Phaeoacremonium aleophilum* | Esca | 26% |
| *Eutypa lata* | Eutypa | 54% |
| *Formitiporia mediteranea* | Esca | 29% |
| *Botryosphaeria obtusa* | Black Dead Arm | 54% |
| *Botryosphaeria dothidea* | Black Dead Arm | 9% |

*Hofstetter V., Casieri L., Viret O. and Gindro K., 2009 - *Esca de la vigne et communauté fongique* - Revue Suisse Viticulture Arboriculture - Changins Vol 41 (4) 247-253

Formulated products are diluted in sterilized dematerialized water at the desired concentration and added to malt agar medium. Fluopyram and penflufen were used as a soluble concentrate formulation formulation containing 100 g/l active ingredient (SC 100), Bixafen as a emulsifiable concentrate formulation containing 200 g/l active ingredient (EC 200), and tebuconazole as a oil in water emulsion formulation containing 250 g/l active ingredient (EW 250). The medium containing the product to be tested is poured in 90 mm diameter Petri dishes. Each dish is then inoculated using a 5 mm diameter mycelium plug taken, using a cork borer, from the active growing edge of a colony.

Inoculated Petri dishes are then incubated at 22° C. with a photoperiod of 12 h. The incubation period corresponds to the time required for the fungus to invade the entire surface of the growth medium. At that time, mycelium growth is evaluated by calculating the mean of two perpendicular measure of the colony diameter. A percentage of efficacy is then calculated (Abbott formula).

The concentration of 50 ppm corresponds approximately to about 50 g/ha when an application amount of 1000 l water per hectare is used.

Results

Fluopyram, Bixafen and Penflufen showed a significant reduction at 50 ppm of several fungi belonging to the community usually found in plants showing Esca symptoms. The test is validated by the level of efficacy of already known fungicides, Tebuconazole at 50 ppm and Flutriafol+Carbendazime.

| Fungi community of Esca symptoms | Group | Presence in infected plants* | In Vitro Efficacy Mycellium** Fluopyram 50 ppm | In Vitro Efficacy Mycellium** Penflufen 50 ppm | In Vitro Efficacy Mycellium** Bixafen 50 ppm | In Vitro efficacy Mycellium** Tebuconazole 50 ppm | In Vitro efficacy Mycellium** Flutriafol + Carbendazime (Escudo) |
|---|---|---|---|---|---|---|---|
| *Phaemoniella chlamydospora* | Ascomycete | 84% | 59% | 75% | 100% | 100% | 100% |
| *Phaeoacremonium aleophilum* | Ascomycete | 26% | 35% | 62% | 69% | 100% | 100% |

| Fungi community of Esca symptoms | Group | Presence in infected plants* | In Vitro Efficacy Mycellium** Fluopyram 50 ppm | In Vitro Efficacy Mycellium** Penflufen 50 ppm | In Vitro Efficacy Mycellium** Bixafen 50 ppm | In Vitro efficacy Mycellium** Tebuconazole 50 ppm | In Vitro efficacy Mycellium** Flutriafol + Carbendazime (Escudo) |
|---|---|---|---|---|---|---|---|
| Eutypa lata | Ascomycete | 54% | 61% | 83% | 100% | 100% | 100% |
| Formitiporia mediteranea | Basidiomycete | 29% | 10% | 100% | 100% | 100% | 76% |
| Botryosphaeria obtusa | Ascomycete | 54% | 65% | 65% | 85% | 100% | 100% |
| Botryosphaeria dothidea | Ascomycete | 9% | 55% | 64% | 86% | 100% | 100% |

The invention claimed is:

1. A method for controlling a wood disease in grape plants or grape plant parts, comprising treating a wood disease-infected grape plant, grape plant part, and/or grape plant grown from grafts and/or cuttings with fluopyram, wherein
    (i) the fluopyram is applied at an application rate of 0.05 to 0.5 kg/ha to the grape plant, grape plant part, and/or grape plant grown from grafts and/or cuttings, and
    (ii) the wood disease is selected from the group consisting of *Esca* and *Eutypa*.

2. A method according to claim 1, wherein the disease *Esca* is controlled.

3. A method according to claim 1, wherein the disease *Eutypa* is controlled.

4. The method according to claim 1, wherein one or more of *Phaemoniella chlamydospora, Phaeoacremonium aleophilum, Formitiporia mediteranea, Eutypa lata, Botryosphaeria obtusa*, or *Botryosphaeria dothidea* is controlled.

5. The method according to claim 1, wherein *Eutypa lata* is controlled.

* * * * *